United States Patent
Naftail et al.

(10) Patent No.: US 9,958,670 B2
(45) Date of Patent: May 1, 2018

(54) SCANNING SYSTEM AND METHOD FOR SCANNING AN OBJECT

(71) Applicant: APPLIED MATERIALS ISRAEL LTD., Rehovot (IL)

(72) Inventors: Ron Naftail, Shoham (IL); Boris Golberg, Ashdod (IL); Rami Elichai, Ashkelon (IL)

(73) Assignee: Applied Materials Israel Ltd., Rehovot (IL)

( * ) Notice: Subject to any disclaimer, the term of this patent is extended or adjusted under 35 U.S.C. 154(b) by 19 days.

(21) Appl. No.: 15/270,311

(22) Filed: Sep. 20, 2016

(65) Prior Publication Data

US 2018/0081166 A1    Mar. 22, 2018

(51) Int. Cl.
| | |
|---|---|
| H01J 40/14 | (2006.01) |
| G02B 26/10 | (2006.01) |
| G02B 27/09 | (2006.01) |
| G01N 21/95 | (2006.01) |
| G01N 21/88 | (2006.01) |

(52) U.S. Cl.
CPC ......... *G02B 26/10* (2013.01); *G01N 21/8806* (2013.01); *G01N 21/9501* (2013.01); *G02B 27/0966* (2013.01); *G01N 2201/105* (2013.01)

(58) Field of Classification Search
CPC . G02B 26/123; G02B 26/124; G01N 21/9501
USPC .................... 250/221, 234; 356/237.2, 237.5
See application file for complete search history.

(56) References Cited

U.S. PATENT DOCUMENTS 9,535,014 B1 *  1/2017 Feldman ............ G01N 21/9501

* cited by examiner

Primary Examiner — Kevin Pyo
(74) Attorney, Agent, or Firm — Kilpatrick Townsend & Stockton LLP

(57) ABSTRACT

A scanning system that includes an illumination module that is configured to scan, at a first direction, an elongated radiation spot over an object; and a collection module that is configured to (a) collect a collected radiation beam from the object, and (b) optically manipulate the collected radiation beam to provide a counter-scan beam is directed towards a set of detection units and has a focal point that is positioned at a same location regardless of the propagation of the elongated radiation spot along the first direction.

15 Claims, 8 Drawing Sheets

SCANNING SYSTEM AND METHOD FOR SCANNING AN OBJECT

BACKGROUND

Objects such as semiconductor wafers may be inspected by various inspection systems.

There is a growing need to provide high throughput scanning systems.

The information included in this background section of the specification, including any reference cited herein and any description or discussion thereof, is included for technical reference purposes only and is not to be regarded as a subject matter by which the scope of the invention is to be bound.

SUMMARY

This summary is neither an extensive nor exhaustive overview of the invention and its various embodiments. It is intended neither to identify key or critical elements of the invention nor to delineate the scope of the invention but to present selected concepts of the invention in a simplified form as an introduction to the more detailed description presented below. As will be appreciated, other embodiments of the invention are possible utilizing, alone or in combination, one or more of the features and aspects set forth above or described in detail below.

A scanning system that may include an illumination module that may be configured to scan, at a first direction, an elongated radiation spot over an object; and a collection module that may be configured to (a) collect a collected radiation beam from the object, and (b) optically manipulate the collected radiation beam to provide a counter-scan beam may be directed towards a set of detection units and may have a focal point that may be positioned at a same location regardless of the propagation of the elongated radiation spot along the first direction.

The scanning system may include the set of detection units, wherein at a given point in time, different detections units of the set of detection units collect different portions of the counter-scan beam.

The length of a field of view of each detection unit of the set of detection units, as imaged on the object, may equal a maximal width of the elongated radiation spot.

The elongated radiation spot may have an elliptical shape.

The front ends of the set of the detection units may be arranged in a column.

The front ends of the set of the detection units may be positioned in a front end plane. A length of the column may equal a length of a spot of the counter-scan beam at the front end plane.

The first direction may be oriented by ninety degrees to the longitudinal axis of the elongated radiation spot.

The illumination module may be configured to scan, at the first direction, multiple elongated radiation spots over the object; and wherein the collection module may be configured to (a) collect multiple collected radiation beams from the object; and (b) optically manipulate the multiple collected radiation beams to provide multiple counter-scan beams that may be directed towards multiple sets of detection units and have a focal point that may be positioned at a same location regardless of the propagation of the multiple elongated radiation spots along the first direction.

Each set of detection unit may be configured to receive a single counter-scan beam.

The multiple elongated radiation spots may be parallel to each other and may be spaced apart from each other only along a direction that may be parallel to a longitudinal axis of each one of the elongated radiation spots.

The multiple elongated radiation spots may be parallel to each other and may be spaced apart from each other along a direction that may be parallel to a longitudinal axis of each one of the elongated radiation spots and along the first direction.

The front ends of each set of the detection units may be arranged in a column.

The front ends of the set of each set of the detection units may be positioned in a front end plane; wherein a length of the column equals a length of a spot of the counter-scan beam at the front end plane.

The first direction may be oriented to a longitudinal axis of the elongated radiation spot.

There may be provided a method for scanning an object, the method may include scanning, by an illumination module, and at a first direction, an elongated radiation spot over an object; collecting, by a collection module, a collected radiation beam from the object; and optically manipulating the collected radiation beam to provide a counter-scan beam may be directed towards a set of detection units and may have a focal point that may be positioned at a same location regardless of the propagation of the elongated radiation spot along the first direction.

Numerous other aspects may be provided in accordance with these and other embodiments of the invention. Other features and aspects of embodiments of the present invention will become more fully apparent from the following detailed description, the appended claims, and the accompanying drawings.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the accompanying drawings:

FIG. 1 is a top view of an example of an elongated radiation spot and an object;

FIG. 2 illustrates an example of an object and a scanning system;

FIG. 3 illustrates an example of an object and a scanning system;

FIG. 4 illustrates various examples of elongated radiation spots and field of views of different detection units as imaged on the object;

FIG. 5 illustrates an example of an object, multiple elongated radiation spots and multiple optic fibers of multiple sets of detection units;

FIG. 6 illustrates an example of an object, multiple elongated radiation spots and multiple optic fibers of multiple sets of detection units;

FIG. 7 illustrates an example of a method; and

FIG. 8 illustrates an example of a method.

DETAILED DESCRIPTION

Figure 1:
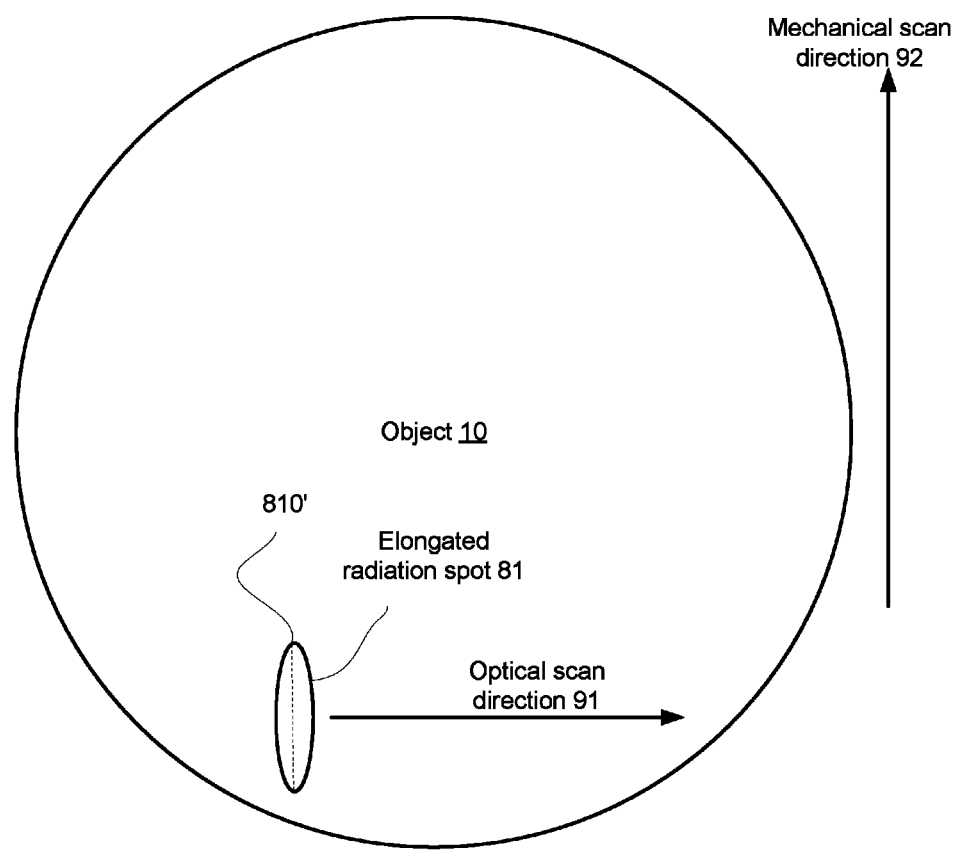

The following detailed description is of exemplary embodiments of the invention but the invention is not limited thereto, as modifications and supplemental structures may be added, as would be apparent to those skilled in the art. In particular, but without limitation, while an exemplary embodiment may be disclosed with regard to a high throughput elliptical light spot optical inspection of a specimen that may be a semiconductor wafer, photomask or the like, it would be readily apparent to one skilled in the art that the teachings are readily adaptable to semiconductor photolithography stepper tools. While a high throughput elliptical light spot optical inspection system is depicted and described in details herein below, the principles of the present invention are applicable to both types of semiconductor process tools and systems. As would be understood by one skilled in the art, both types of systems may be utilized in accordance with the present invention.

Moreover, the principles of the present invention high throughput elliptical light spot optical scanning systems may be applicable to any optical inspection system, and semiconductor process tools are depicted and described in details herein below as non-limiting example. The principles of the present invention high throughput optical scanning systems are applicable to display inspection system, for example, and the like.

While an exemplary embodiment may be disclosed with regard to the inspection of a subject surface by detecting reflected light using a light source and detecting unit that are disposed on a common side of an object ("reflective system"), it would be readily apparent to one skilled in the art that the teachings are readily adaptable to the inspection of an object by detecting transmitted light with a detecting unit that is on a side of an object opposite to that of the light source (a "transmissive system").

As used herein, the words "photomask", "mask" and "reticle" are interchangeable and mean an opaque plate with holes or transparencies configured to allow light to shine through in a defined pattern.

In the description and claims of the application, each of the words "comprise" "include" and "have", and forms thereof, are not necessarily limited to members in a list with which the words may be associated.

There may be provided a scanning system. The scanning system may include an illumination module that is configured to scan, at a first direction, an elongated radiation spot over an object; and a collection module that is configured to (a) collect a collected radiation beam from the object, and (b) optically manipulate the collected radiation beam to provide a counter-scan beam is directed towards a set of detection units and has a focal point that is positioned at a same location regardless of the propagation of the elongated radiation spot along the first direction.

Using a set of detection units increases the throughput of the scanning system. The optical manipulation of the collected radiation beam causes the beam to be static (from a point of view of the set of detector)—thus reducing artifacts and increasing the quality of data acquired by the set of detectors.

The throughput of the scanning system may further increase when the illumination module scans multiple elongated radiation spots simultaneously. The scanning causes multiple collected radiation beams to impinge from the object and to be collected by the collection module. Different collected radiation beams are detected by different sets of detection units.

The elongated radiation spot may be elliptical, rectangular or have any other shape.

The elongated radiation spot may impinge on the object at a location that is within the field of view of the collection module or may impinge on the object at a location that is outside the field of view of the collection module.

FIG. 1 is a top view of an example of an elongated radiation spot 81 and an object 10. The object 10 is moved along a mechanical scan direction 92 while the elongated radiation spot 81 is scanned along optical scan direction 91.

In FIG. 1 the mechanical scan direction 92 is normal to the optical scan direction 91—but the mechanical scan direction 92 may be oriented to the optical scan direction 91 by other angles.

In FIG. 1 the optical scan direction 91 is normal to a longitudinal axis 810' of the elongated radiation spot 81—but the longitudinal axis 810' may be oriented to the optical scan direction 91 by other angles.

Figure 2:
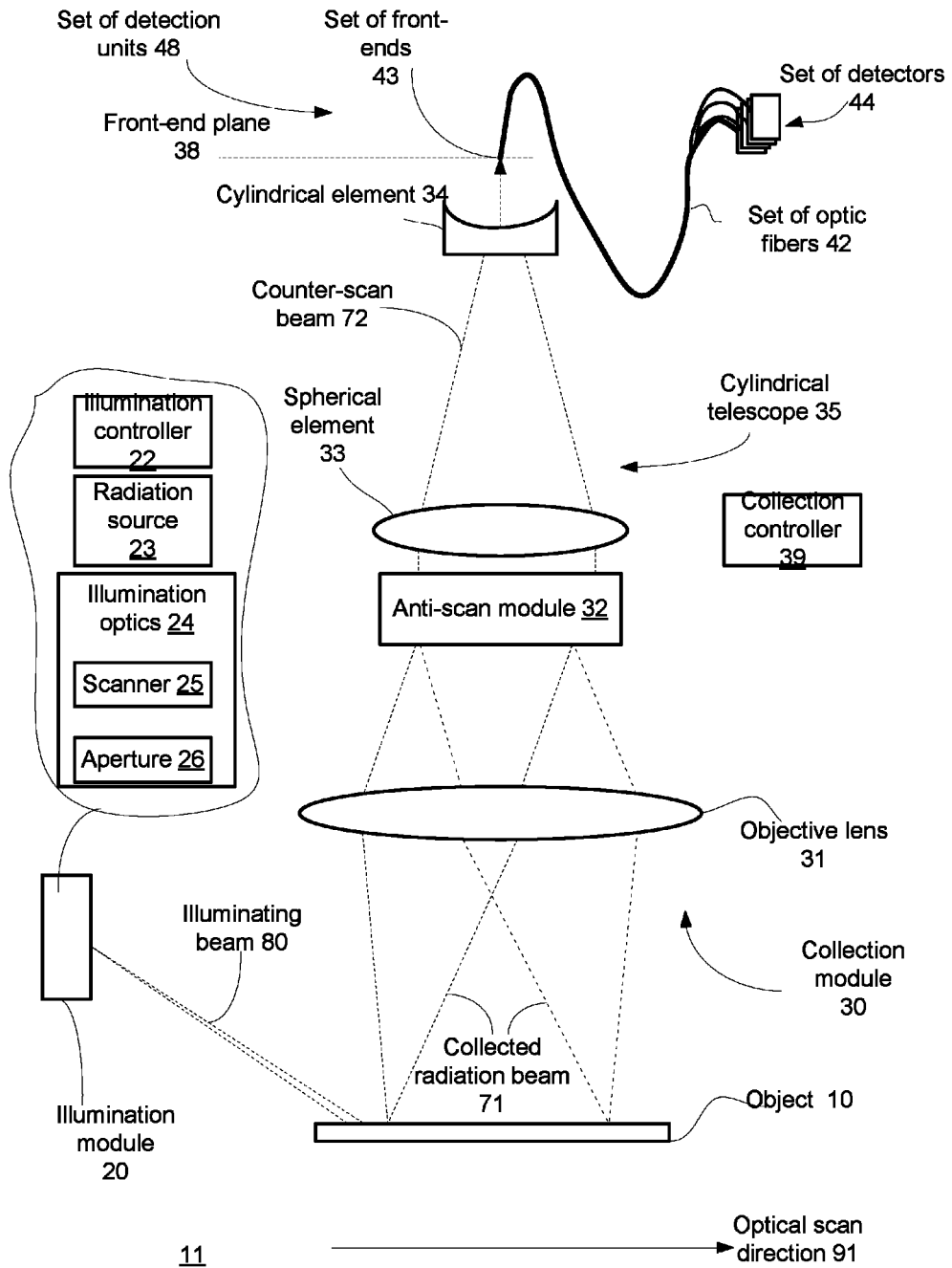
Figure 3:
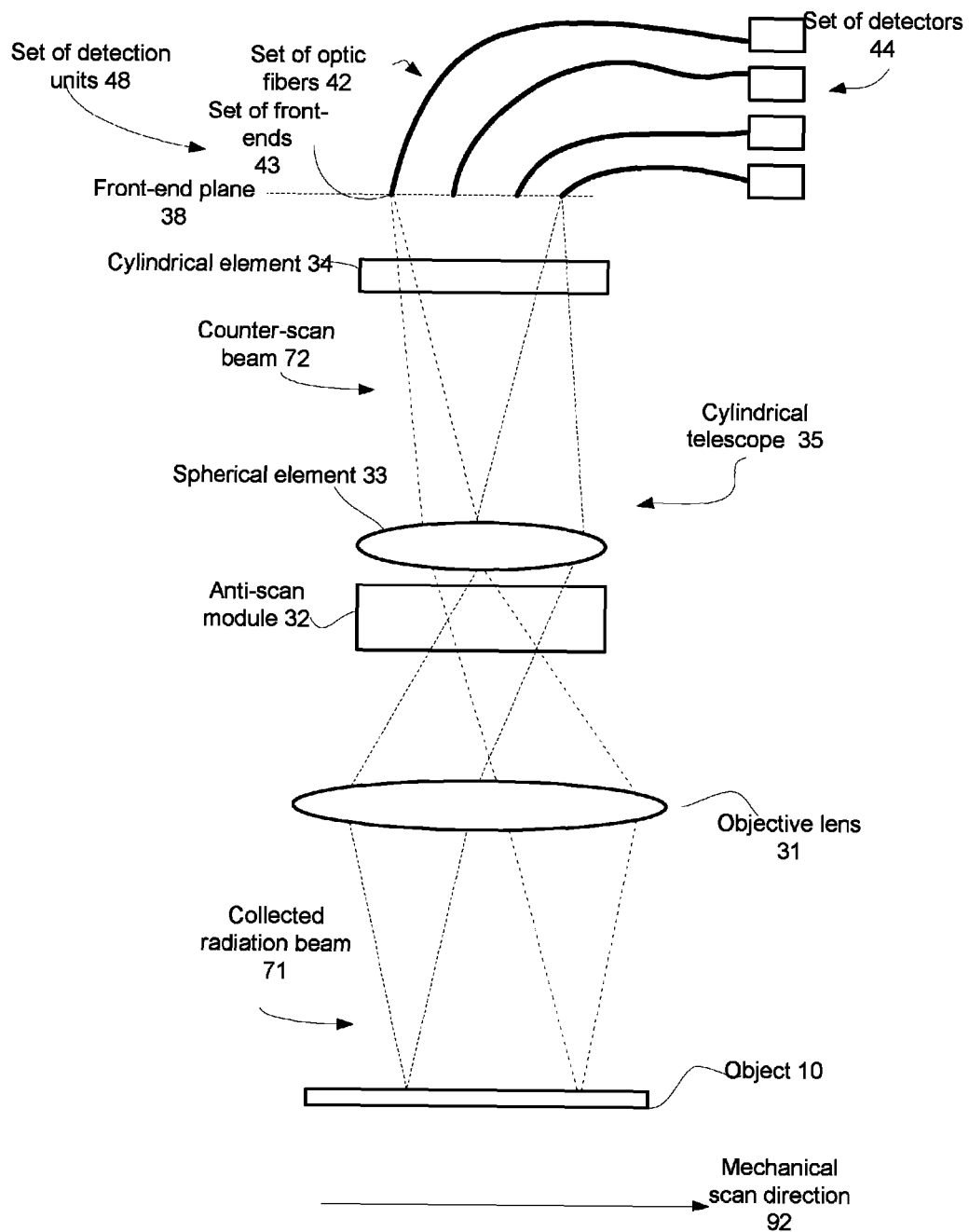

FIG. 2 and FIG. 3 illustrate object 10 and scanning system 11 from the optical scan direction 91 and from the mechanical scan direction 92, respectively.

Scanning system 11 includes an illumination module 20 and a collection module 30.

Illumination module 20 is configured to scan the elongated radiation spot 81 along the optical scan direction 91.

In FIG. 2 the illumination module 20 is illustrated as including an illumination controller 22, radiation source 23, illumination optics 24. Illumination optics 24 is illustrated as including scanner 25 and aperture 26.

Illumination controller 22 is configured to control the operation of illumination module 20.

Radiation source 23 may generate one or more radiation beams. A radiation beam may be, for example, a light beam, an ultraviolet (UV) beam, a deep UV beam, an extreme UV beam, and the like.

Illumination optics 24 is configured to perform at least one operation out of (a) determine (for example by aperture 26—which may be an elliptical aperture or any other elongated shape aperture) the shape of the elongated radiation spot that will impinge on the object, (b) directing the radiation beam onto the object, (c) scan the radiation beam (and thus scan the elongated radiation spot) on the object—at the optical scan direction (for example—by scanner 25), (d) determine any other optical parameter of the elongated radiation spot—such as frequency range, polarization, and the like.

In FIGS. 2 and 3 the collection module 30 is illustrated as including an objective lens 31, anti-scan module 32, a cylindrical telescope 35 that includes spherical element 33 and cylindrical element 34, collection controller 39 and set of detection units 48 that include a set of detectors 44, and a set of optic fibers 42 that have a set of front ends 43.

Each optic fiber of the set of optic fibers 42 has a front end that is located in a front end plane 38—and the set of front ends 43 form a column in the front end plane. The longitudinal axis of the column is normal to the page of FIG. 2 and is within the page of FIG. 3.

Objective lens 31 collects collected radiation beam 71 that results from the scanning of the elongated radiation spot on object 10. Collected radiation beam 71 moves during the scanning of the elongated radiation spot.

Anti-scan module 32 is configured to counter the movement of the collected radiation beam to provide a counter-scan beam 72 that is directed towards set of detection units 48 and has a focal point that is positioned at a same location regardless of the propagation of the elongated radiation spot 81 along the first direction.

The counter-scan beam 72 remains static, regardless the scanning of the elongated radiation spot, at front end plane 38.

The cylindrical telescope 35 collects the counter-scan beam 72, may magnify the counter-scan beam and uses the cylindrical element 34 to convert a circular part of the counter-scan beam (corresponding to a circular field on view on object 10) to an elliptical portion that is directed towards the elliptical shaped set of front ends 43. The elongated axis of each elliptical shaped front end is parallel to the page of FIG. 3 and normal to the page of FIG. 2.

Other shaped front-ends may require using other optical components. The cylindrical telescope 35 is merely an example of a telescope or any magnifying optical arrangement.

Set of detection units 48 includes set of detectors 44 and set of optic fibers 42. Set of detectors 44 and set of optic fibers 42 are optically coupled to each other. Set of optic fibers 42 that have a set of front ends 43.

The set of detectors 44 may be arranged in a column although the set of detector 44 may be arranged in other arrangement. It may be beneficial to use optic fibers 42 that have the same optical characteristics—and may have the same length.

Collection controller 39 is configured to control the operation of the collection module 30. Especially, the illumination controller 22 and the collection controller 39 (or only the collection controller) should guarantee that the anti-scan module 32 counters the scanning of the scanner 25.

The anti-scan module 32 may include a rotating drum or polygon, an acousto-optic element, and the like.

Figure 4:
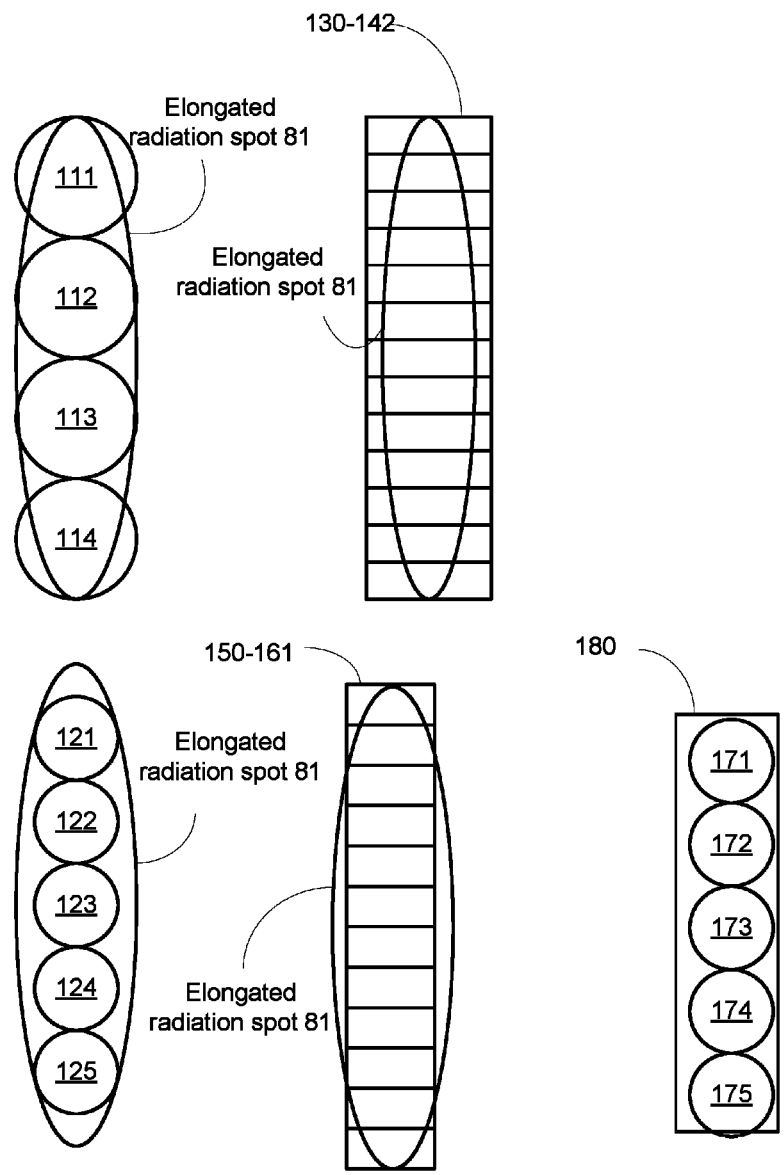

FIG. 4 illustrates various examples of elongated radiation spots and field of views of different detection units as imaged on the object. It is noted that the elongated radiation spot may have any elongated shape, that the field of view of the different detection units may have any shape and that there may different spatial relationships between the elongated radiation spot and the fields of view. It is beneficial that the different fields of view, given the optical scan direction, do not form gaps in the coverage of the object.

Elongated radiation spot 81 has an elliptical shape and can be at least partially covered by:

(a) Circular fields of view 111, 112, 113, 114 that have a diameter that equals the maximal width of elongated radiation spot 81.

(b) Circular fields of view 121, 122, 123, 124 and 125 that have a diameter that is smaller than the maximal width of elongated radiation spot 81.

(c) Rectangular field of views 130-142 that have a length that exceeds the maximal width of elongated radiation spot 81.

(d) Rectangular field of views 150-161 that have a length that is smaller than the maximal width of elongated radiation spot 81.

Elongated radiation spot 180 has a rectangular shape and can be at least partially covered by circular fields of view 171, 172, 173, 174 and 175 that have a diameter that is smaller than the width of elongated radiation spot 180.

Figure 5:
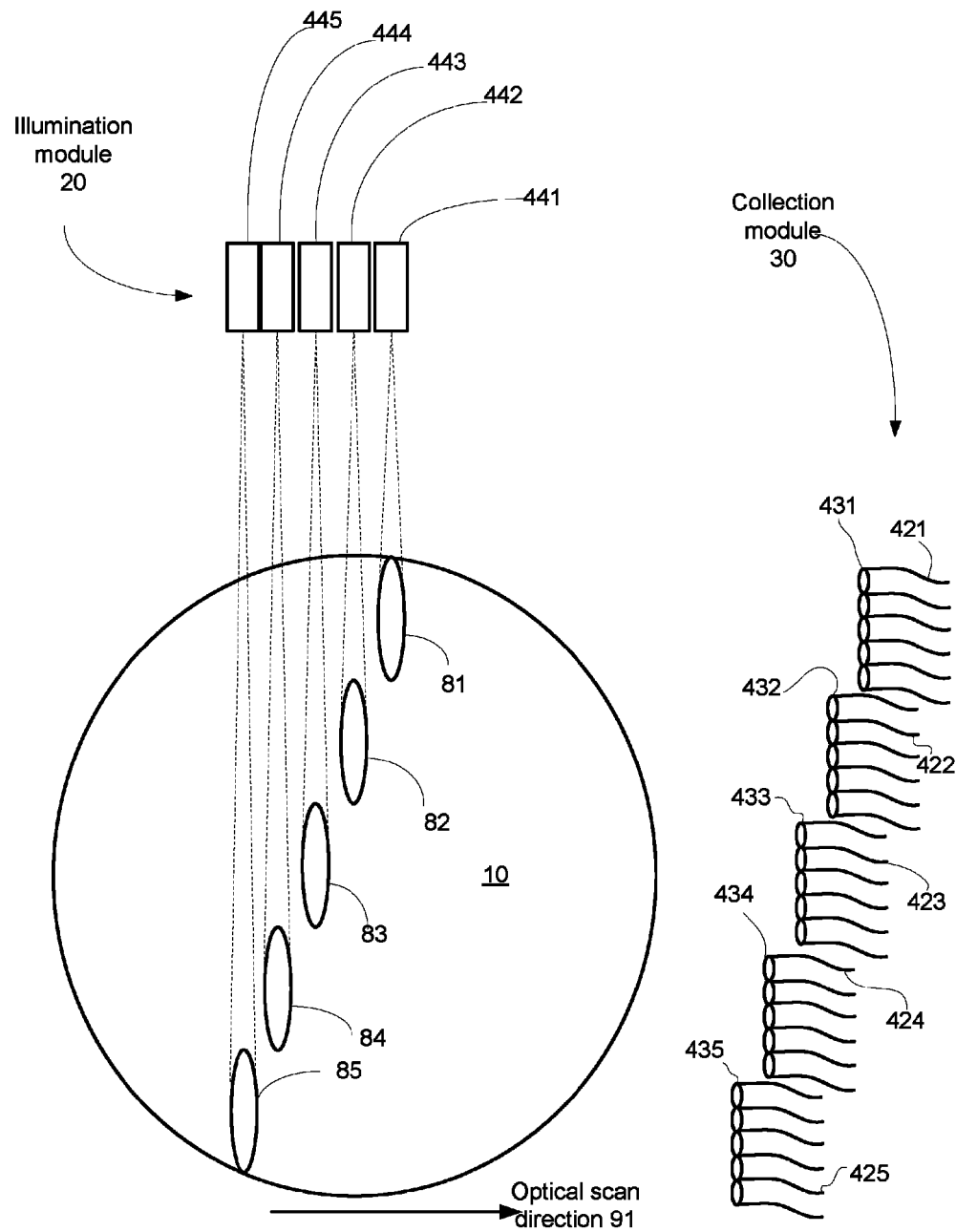

FIG. 5 illustrates an example of object 10, illumination module 20 multiple elongated radiation spots 81, 82, 83, 84 and 85 and multiple optic fibers of multiple sets of detection units.

For simplicity of explanation only some of the components of the collection module 30 are shown.

Illumination module 20 includes multiple illumination units 441, 442, 443, 444 and 445 that are configured to generate multiple elongated radiation spots 81, 82, 83, 84 and 85 that may scan the object at the same time—thereby increasing the throughput of scanning system 11.

Each one of illumination units 441, 442, 443, 444 and 445 may include a radiation source and illumination optics.

Alternatively, the illumination units 441, 442, 443, 444 and 445 may share a radiation source and/or may share one or more optical illumination components.

For example—the illumination units 441, 442, 444 and 445 may share a radiation source, a scanner. In this case the illumination optics may include a splitter (such as a Bragg diffraction grid) for splitting a single illuminating beam to multiple illuminating beams, the multiple illumination beams impinge on object 10 and form (on object 10) multiple elongated radiation spots 81, 82, 83, 84 and 85 on object 10.

Elongated radiation spots 81, 82, 83, 84 and 85 are staggered—they are spaced apart on the optical scan direction 91 and on the mechanical scan direction 92.

Each elongated spot of elongated radiation spots 81, 82, 83, 84 and 85 is collected by a set of detection units out of five sets of detection units. The five sets of detection units have five sets of optical fibers 421, 422, 423, 424 and 425 that have five sets of front-ends 431, 432, 433, 434 and 435 that are arranged, in the front-end plane 38 as five staggered columns.

Figure 6:
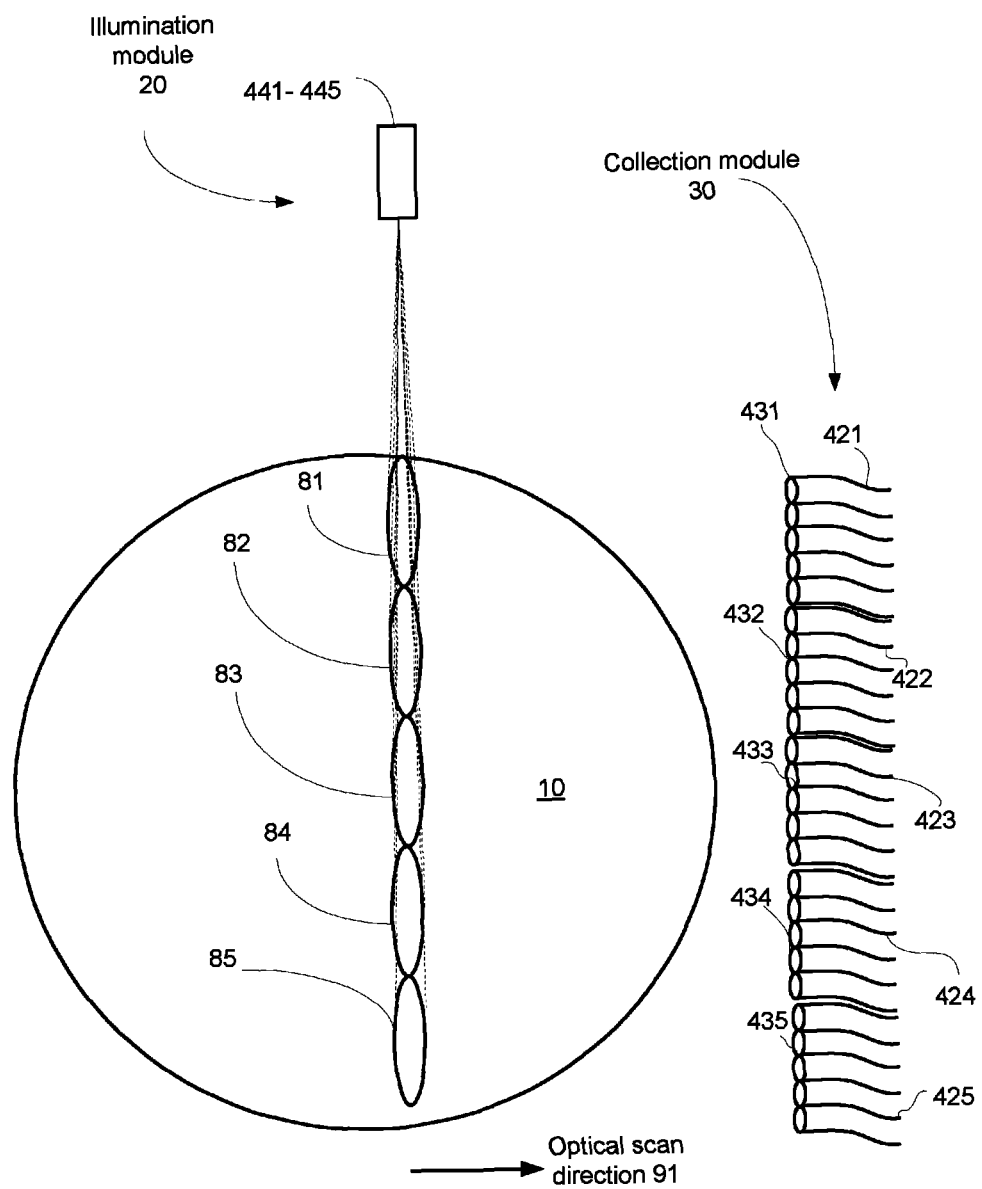

FIG. 6 illustrates an example of object 10, illumination module 20 multiple elongated radiation spots 81, 82, 83, 84 and 85 and multiple optic fibers of multiple sets of detection units.

In FIG. 6 the multiple elongated radiation spots 81, 82, 83, 84 and 85 are arranged in a column—and the five sets of front-ends 431, 432, 433, 434 and 435 that are arranged, in the front-end plane 38 as a single column.

Figure 7:
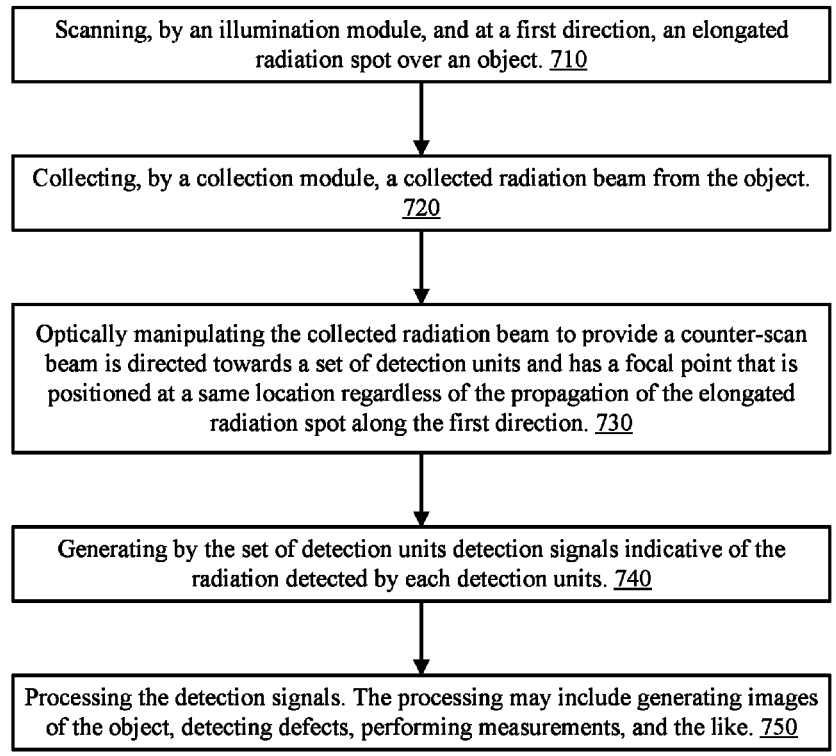

FIG. 7 illustrates method 700 according to an embodiment of the invention.

Method 700 may start by step 710 of scanning, by an illumination module, and at a first direction, an elongated radiation spot over an object.

The first direction may be oriented by any angle (for example ninety degrees) to the longitudinal axis of the elongated radiation spot.

Step 710 may also include mechanically moving the object in relation to the illumination module.

Step 710 may be followed by step 720 of collecting, by a collection module, a collected radiation beam from the object.

Step 720 may be followed by step 730 of optically manipulating the collected radiation beam to provide a counter-scan beam is directed towards a set of detection units and has a focal point that is positioned at a same location regardless of the propagation of the elongated radiation spot along the first direction.

A length of a field of view of each detection unit of the set of detection units, as imaged on the object, may equal a maximal width of the elongated radiation spot, may be smaller than the maximal width of the elongated radiation spot or may exceed the maximal width of the elongated radiation spot.

The elongated radiation spot may have an elliptical shape, a rectangular shape or any other elongated shape.

Front ends of the set of the detection units may be arranged in a column.

Front ends of the set of the detection units are positioned in a front end plane. The length of the column may equal a length of a spot of the counter-scan beam at the front end plane.

Step 730 may be followed by step 740 of generating, by the set of detection units, detection signals indicative of the radiation detected by each detection units.

Step 740 may be followed by step 750 of processing the detection signals. The processing may include generating images of the object, detecting defects, performing measurements, and the like.

Step 720 may include collecting, at a given point in time, different portions of the counter-scan beam by different detections units of the set of detection units. For example, FIG. 3 illustrates different portions of the counter-scan beam.

Figure 8:
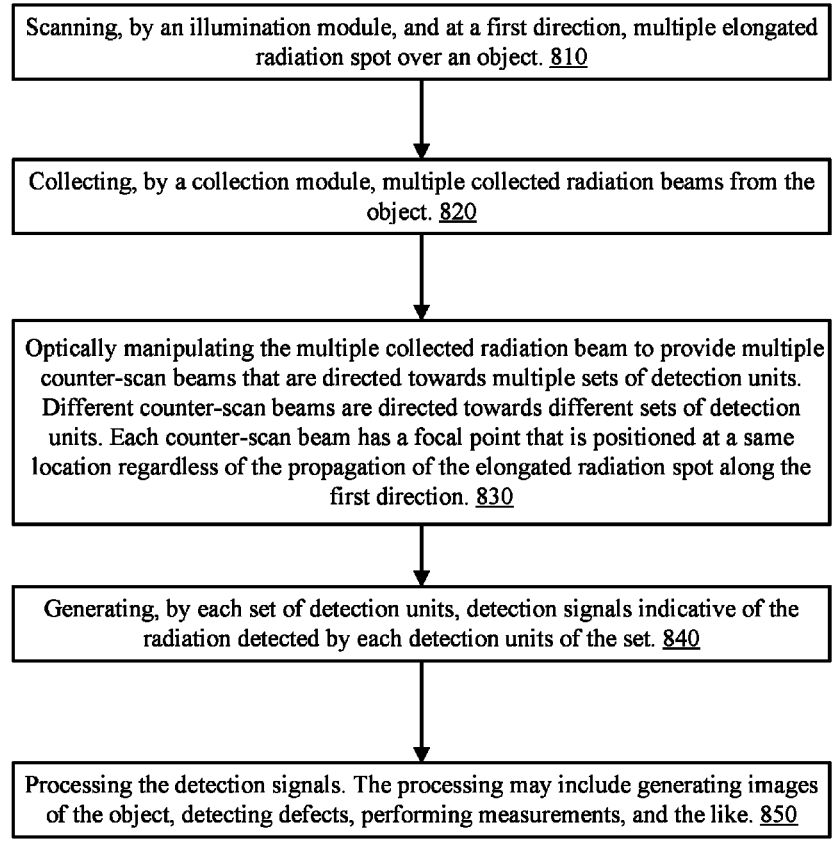

FIG. 8 illustrates method 800 according to an embodiment of the invention.

Method 800 may start by step 810 of scanning, by an illumination module, and at a first direction, multiple elongated radiation spot over an object.

Step 810 may be followed by step 820 of collecting, by a collection module, multiple collected radiation beams from the object.

Step 820 may include collecting, at a given point in time, different portions of the counter-scan beam by different detections units of each set of detection units. For example, FIG. 3 illustrates different portions of the counter-scan beam.

Step 820 may be followed by step 830 of optically manipulating the multiple collected radiation beam to provide multiple counter-scan beams that are directed towards multiple sets of detection units. Different counter-scan beams are directed towards different sets of detection units. Each counter-scan beam has a focal point that is positioned at a same location regardless of the propagation of the elongated radiation spot along the first direction.

A length of a field of view of each detection unit of each set of detection units, as imaged on the object, may equal a maximal width of a corresponding elongated radiation spot, may be smaller than the maximal width of the corresponding elongated radiation spot or may exceed the maximal width of the corresponding elongated radiation spot.

Each elongated radiation spot may have an elliptical shape, a rectangular shape or any other elongated shape.

Front ends of each set of the detection units may be arranged in a column.

Front ends of each set of the detection units are positioned in a front end plane. The length of the column may equal a length of a spot of the corresponding counter-scan beam at the front end plane.

Step 830 may be followed by step 840 of generating, by each set of detection units, detection signals indicative of the radiation detected by each detection units of the set.

Step 840 may be followed by step 850 of processing the detection signals. The processing may include generating images of the object, detecting defects, performing measurements, and the like.

While a number of exemplary aspects and embodiments have been discussed above, those of skill in the art will recognize certain modifications, permutations, additions and sub combinations thereof. It is therefore intended that the following appended claims and claims hereafter introduced be interpreted to include all such modifications, permutations, additions and sub-combinations as are within their true spirit and scope.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description. While preferred embodiments of the present invention have been shown and described, it should be understood that various alternatives, substitutions, and equivalents can be used, and the present invention should only be limited by the claims and equivalents thereof.

What is claimed is:

1. A scanning system, comprising:
   an illumination module that is configured to scan, at a first direction, an elongated radiation spot over an object; and
   a collection module that is configured to (a) collect a collected radiation beam from the object, and (b) optically manipulate the collected radiation beam to provide a counter-scan beam that is directed towards a set of detection units and has a focal point that is positioned at a same location regardless of a propagation of the elongated radiation spot along the first direction.

2. The scanning system according to claim 1, further comprising the set of detection units, wherein at a given point in time, different detections units of the set of detection units collect different portions of the counter-scan beam.

3. The scanning system according to claim 1, wherein a length of a field of view of each detection unit of the set of detection units, as imaged on the object, equals a maximal width of the elongated radiation spot.

4. The scanning system according to claim 1, wherein the elongated radiation spot has an elliptical shape.

5. The scanning system according to claim 1, wherein front ends of the set of the detection units are arranged in a column.

6. The scanning system according to claim 5, wherein the front ends of the set of the detection units are positioned in a front end plane; wherein a length of the column equals a length of a spot of the counter-scan beam at the front end plane.

7. The scanning system according to claim 1, wherein the first direction is oriented by ninety degrees to a longitudinal axis of the elongated radiation spot.

8. The scanning system according to claim 1 wherein the illumination module is configured to scan, along the first direction, multiple elongated radiation spots over the object; and wherein the collection module is configured to (a) collect multiple collected radiation beams from the object; and (b) optically manipulate the multiple collected radiation beams to provide multiple counter-scan beams that are directed towards multiple sets of detection units and have a focal point that is positioned at a same location regardless of a propagation of the multiple elongated radiation spots along the first direction.

9. The scanning system according to claim 8 wherein each set of the detection units is configured to receive a single counter-scan beam.

10. The scanning system according to claim 8 wherein the multiple elongated radiation spots are parallel to each other and are spaced apart from each other only along a direction that is parallel to a longitudinal axis of each one of the elongated radiation spots.

11. The scanning system according to claim 8 wherein the multiple elongated radiation spots are parallel to each other and are spaced apart from each other along a direction that is parallel to a longitudinal axis of each one of the elongated radiation spots and along the first direction.

12. The scanning system according to claim 8, wherein front ends of each set of the detection units are arranged in a column.

13. The scanning system according to claim 8, wherein front ends of each set of the detection units are positioned in a column and a front end plane; wherein a length of the column equals a length of a spot of the counter-scan beam at the front end plane.

14. The scanning system according to claim 1 wherein the first direction is oriented to a longitudinal axis of the elongated radiation spot.

15. A method for scanning an object, the method comprising:
   scanning, by an illumination module and at a first direction, an elongated radiation spot over an object;
   collecting, by a collection module, a collected radiation beam from the object; and
   optically manipulating the collected radiation beam to provide a counter-scan beam that is directed towards a set of detection units and has a focal point that is positioned at a same location regardless of a propagation of the elongated radiation spot along the first direction.

* * * * *